United States Patent [19]

Yau-Young

[11] Patent Number: 4,952,405
[45] Date of Patent: Aug. 28, 1990

[54] METHOD OF TREATING *M. AVIUM* INFECTION

[75] Inventor: Annie Yau-Young, Los Altos, Calif.

[73] Assignee: Liposome Technology, Inc., Menlo Park, Calif.

[21] Appl. No.: 260,258

[22] Filed: Oct. 20, 1988

[51] Int. Cl.$^5$ .............................................. A61K 9/127
[52] U.S. Cl. .................. 424/423; 428/402.2; 424/450; 514/37; 514/922
[58] Field of Search ...................... 424/450; 514/37, 78

[56] References Cited

U.S. PATENT DOCUMENTS

| 4,588,578 | 5/1986 | Fountain et al. | 428/402.2 |
| 4,610,868 | 9/1986 | Fountain et al. | 264/4.1 X |
| 4,731,210 | 3/1988 | Weder et al. | 264/4.3 |

FOREIGN PATENT DOCUMENTS

85/00515 2/1985 PCT Int'l Appl. ................. 424/450

OTHER PUBLICATIONS

*Chem. Abstracts*, vol. 106, No. 3, Abstract 15636s, Wallace et al., "Susceptibility of Slowly Growing Mycobacteria . . . ", 1986 in *J. Clin. Microbiol.* 24(6), 149-155.
*Chem. Abstracts*, vol. 109, No. 3, Abstract 20136w, Davis et al., "In Vitro Susceptibility of Mycobacterium Avium Complex . . . ", 1987 in *Diagn. Microbiol Infect. Dis.* 8(3), 149-155.
*Chem. Abstracts*, vol. 107, No. 25, Abstract 232920f, Bermudez et al., "Intracellular Killing of Nycobacterium Avium Complex . . . ", 1987 in *J. Infect. Dis.*, 156(3), 510-513.
*Chem. Abstracts*, vol. 110, No. 22, Abstract 199086w, Saito et al., "Therapeutic Efficacy of Liposome-Entrapped . . . ", 1989 in *Antimicrob. Agents Chemother*, 33(4), 429-433.
Duzganes et al., "Enhanced Effect of Liposome Encapsulated Amikacin . . . ", 1988; *Antimicrob. Agents Chemother*, (32) 1404-1411.
Ginsberg, R., "Treatment of a Model of Gram-Negative Pneumonia with Liposome-Entrapped Gentamicin", 1987; *Therapeutic Applications of Liposomes, Third Princeton-Liposome Conference Proceedings Highlights*, pp. 7-9.
Pattisapu et al., "Comparative Activities of Free and Loposome Encapsulated Amikacin Against Mycobacterium Avium Complex (MAC)", 1988; *J. Cel. Biochem. Supplement* 12B:250.
Scheier et al., "Sustained Release of Liposome Encapsulated Gentamycin . . . ", 1987; *J. Controlled Rel.* (5) 187-192.

*Primary Examiner*—Richard D. Lovering
*Assistant Examiner*—John M. Covert
*Attorney, Agent, or Firm*—Peter J. Dehlinger

[57] ABSTRACT

A method of selectively enhancing efficacy of gentamicin, when used in the treatment of *Mycobacterium avium* Complex (MAC), by intravenous administration of the drug in liposomal form. Gentamicin-liposomes are comparable to amikacinliposomes in activity against MAC infection in the bloodstream and substantially more effective against MAC infection residing in liver and spleen.

4 Claims, 5 Drawing Sheets

METHOD OF TREATING M. AVIUM INFECTION

FIELD OF THE INVENTION

The present invention relates to a method of treating *Mycobacterium avium* Complex (MAC) infection, and more particularly, to a method for treating such infection with gentamicin.

REFERENCES

Armstrong, D., et al, *Ann. Intern. Med.*, 103:738 (1985).
Barlett, G.H., *J. Biol. Chem.*, 234:466 (1959).
Baron, E.J., et al, *Diagn. Microbiol. Infect. Dis.*, 5:215 (1986).
Bermudez, L.E.M., *J. Infect. Dis.*, 156:510 (1987).
Chapman, J., *The Atypical Mycrobacteria and Human Mycrobacteriosis*, Pleneum Pub., N.Y. (1977).
de PonCeri-Morton, C., et al, *Clin. Study No. 64*, Syva, Palo Alto, Calif. (1979).
Falk, G.S., et al, *Am. J. Med.*, 54:801 (1973).
Hawkins, C., et al, *Ann. Int. Med.*, 105:184 (1986).
Juliano, R.L., *Biochem. Biophys. Res. Commun.*, 63(3):651 (1975).
Kiehn, T.E., et al, *J. Chem. Microbiol.*, 2:168 (1985).
Marinetti, G.V., *J. Lipid Res.*, 3:1 (1962).
Szoka, F., et al, *Ann. Rev. Biophys. Bioeng.*, 9:467 (1980).
Yajko, D.M., et al, *Antimicrob. Agents Chemother.*, 32(1):117 (1987).
Young, L.S., et al., *Am. J. Med*, 82(Supp4A):23 (1987)
Young, L.S., et al, *Rev. Infect. Dis.*, 8:1024 (1986).
Young, L.S., *J. Infect. Dis.*, 157(5):863 (1988).
Zimmer, B.L., *AntimiCrob. Agents Chemother.*, 22:148 (1982).

BACKGROUND

*Mycobacterium avium* complex (MAC), also known as *Macobacterium avium intracellulaire* (MAI), is one of the most common systemic gram-positive bacterial infections in patients with AIDS (Armstrong, Young, 1986). MAC infection in humans is associated with infeCtions of the lungs, lymph nodes, skin, bones, soft, tissue, and urinary tract (Chapman, Falk). Current treatment of *M. avium* complex infection in AIDS patients consists of a variety of drug therapies which generally include ansamysin, clofazamine, isoniazid, and amikacin (Hawkins, Kiehn, Zimmer, Young, 1987, 1988, Baron, Bermudez). Typically the drug amikacin is administered intravenously (I.V.) in free-drug form 2-3 times a day until the level of infection is reduced. The patient is then maintained on a lower-dose regimen to keep the infection in check. One of the difficulties in treating the disease, and one reason that combinations of drugs are now used, is that the infection is active both in the bloodstream, where it is susceptible to certain drugs and in macrophages of the liver, spleen and other reticuloendothelial tissue, where the bacteria is protected from the drugs. That is, current therapy is at best only partially effective in the treatment MAC infection.

Among the aminoglycosides, amikacin has been used for treating MAC infection due to its relatively low minimum inhibitory concentration, particularly in the case of certain MAC serotypes. For example, the minimum inhibitory concentration (MIC) of amikacin against MAC 101 serotype 1 is between 2–4 $\mu$g/ml, versus at 36 $\mu$g/ml for gentamicin (Bermudez, L.E.M., et al unpublished data); although it is noted that amikacin and gentamicin have comparable MICs against a serotype 4 strain of MAC of between about 16–32 $\mu$g/ml (Yajko). Gentamicin would therefore not be expected to be effective in vivo since the toxic level of gentamicin is about 12 $\mu$g/ml in the blood, and therefore it is not possible to maintain patients at the inhibitory dose for sustained therapeutic periods. It would be desirable to treat *M. avium* infection in humans with gentamicin, however, because of the relatively low cost of the drug. It would also be desirable to provide, for treating MAC infection both is immune-compromised patients, a therapeutic method which requires less frequent I.V. dosing and is effective against MAC infection in the bloodstream and reticuloendothelial (RES) tissues.

SUMMARY OF THE INVENTION

It is one object of the invention to provide a method of treating *M. avium* infection in humans by I.V. administration of gentamicin.

A more specific object of the method is to provide such a method in which the anti-MAC activity of gentamicin, at a selected dose, is substantially greater than that of amikacin in RES tissue and comparable to that of amikacin in the bloodstream.

The treatment method of the invention is based on the discoveries that gentamicin, when administered in liposome-encapsulated form, has substantially the same activity/dose level against *M avium* infection in treated subjects as amikacin in liposomal form and a substantially higher activity/dose than amikacin-liposomes against MAC infection in RES tissues.

In one aspect, the method of the invention comprises providing a suspension of liposomes containing entrapped gentamicin, and administering a therapeutically effective amount of the suspension (which is below chronic toxicity levels) intravenously to the infected subject. The administering is repeated at selected intervals until the number of viable *M. avium* units in the bloodstream is significantly reduced.

According to one feature of the invention, the amount of gentamicin administered to the subject in the suspension is substantially the same as the amount of amikacin, in liposome--entrapped form, that would be administered intravenously to the subject to achieve a comparable reduction in *M. avium* infection in the bloodstream. At this dose level, the gentamicin-liposomes are up to several fold more active against MAC infection in the liver and spleen than the same dose of amikacin liposomes.

In a preferred embodiment, the gentamicin-liposomes are administered once every 1–3 days, at a dose of about 1–20 mg/kg body weight. The liposomes contain between about 50–80 mole percent phosphatidylcholine and between about 20–50 mole percent cholesterol, and the amount of entrapped gentamicin is about 5–30 mole percent of total lipids.

These and other objects and features of the present invention will become more fully apparent when the following detailed description of the invention is read in conjunction with the accompanying drawings.

DETAILED DESCRIPTION OF THE INVENTION

I. Preparing Gentamicin Liposomes

Figure 1:
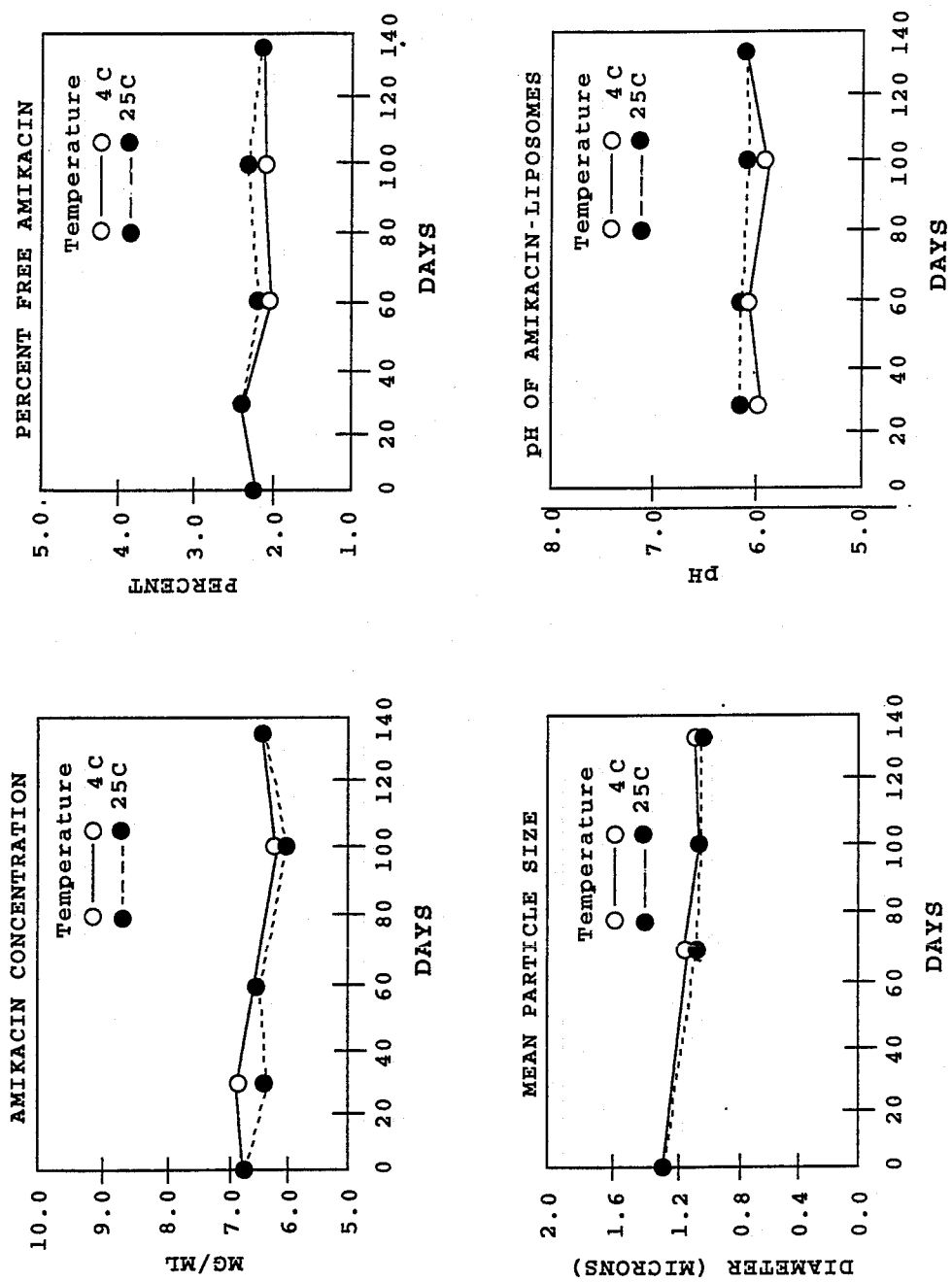
FIGS. 1A–1D are plots, taken over a storage period of 270 days, at 4° C. and 25° C. of (1A) gentamicin concentration; (1B) percent free gentamicin; (1C) mean liposome particle size; and (1D) percent hydrolysis of phospholipid in a gentamicin liposome suspension.

This section describes preferred methods of preparing gentamicin-liposomes for use in the method of the invention and stability characteristics of the liposome formulation.

A. Lipid Components

The liposomes in the composition are formed from standard vesicle-forming lipids, which generally include neutral and negatively charged phospholipids and a sterol, such as cholesterol. The selection of lipids is generally guided by consideration of (a) liposome size, (b) stability of the liposomes in the bloodstream and (c) rate of uptake by macrophages cells of the reticuloendothelial symptom (RES).

Typically, the major lipid component in the liposomes is phosphatidylcholine (PC). PCs having a variety of acyl chain groups of varying chain length and degree of saturation are available or may be isolated or synthesized by well-known techniques. In general, less saturated PCs are more easily sized, particularly when the liposomes must be sized below about 0.3 microns, for purposes of filter sterilization. Methods used in sizing and filter-sterilizing liposomes are discussed below. The acyl chain composition of phospholipid may also affect the stability of liposomes in the blood. One preferred PC is partially hydrogenated egg PC (PH EPC).

Since the gentamicin-liposomes are intended for uptake by MAC-infected macrophages, the lipid components are further selected to enhance liposome uptake by the macrophage cells of the RES. It is known that liposome charge is an important determinant in liposome clearance from the blood, with negatively charged liposomes being taken up more rapidly by the RES (Juliano). Typically, the liposomes are prepared with about 5-15 mole percent negatively charged phospholipids, such as phosphatidylglycerol (PG), phosphatidylserine (PS) or phosphatidylinositol (PI). Added negatively charged phospholipids, such as PG, also serves to prevent spontaneous liposome aggregating, and thus minimize the risk of undersized liposomal aggregate formation.

In addition to neutral phospholipids and negatively charged lipid components, it is generally desirable to include cholesterol or other sterols to enhance membrane stability in the bloodstream. Typically, the amount of cholesterol in the liposomes is between about 20-50 mole percent. One preferred lipid composition, described in Example 1, includes 62 mole percent PH EPC, 33 mole percent cholesterol, and 5 mole percent egg PG.

Additionally, the liposome suspension may include lipid-protective agents which protect lipids and drug components against free-radical and lipid-peroxidative damages on storage. Lipophilic free-radical quenchers, such as alphatocopherol and water-soluble iron-specific chelators, such as ferrioxianine, are preferred. Other lipid components, such as glycolipids and other antigenic lipid components, for use in macrophage targeting, may also be employed.

B. Liposome Preparation

A variety of methods are available for preparing liposomes and these have been reviewed at length by Szoka. One standard method produces multilamellar vesicles (MLVs) of heterogeneous sizes. In this method, the vesicle forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous gentamicin solution and allowed to hydrate, typically over a 15-60 minute period with agitation. The size distribution of the resulting MLVs can be shifted toward smaller sized by hydrating the lipids under more vigorous agitation conditions.

The hydration medium contains gentamicin at a concentration which is desired in the interior volume of the liposomes in the final liposome suspension. Typically the gentamicin solution contains between 10-100 mg/ml in a buffered saline, preferably about pH 6.0.

One preferred method for producing gentamicin liposomes is a high-encapsulation solvent injection system described in co-owned U.S. Pat. No. 4,781,871. Briefly., a Freon TM solution of vesicle-forming lipids is injected into an aqueous gentamicin solution, under conditions in which the Freon TM solvent is removed at substantially the same rate that it is introduced. Solvent injection is continued until a desired liposome concentration, typically about 100-200 and up to 400 $\mu$mol/ml is reached. The method is detailed in Example 1.

C. Liposome Sizing

Following liposome preparation, the liposomes may be sized to achieve a desired size range and relatively narrow distribution of liposome sizes. One preferred size range is about 0.2-0.4 microns, which allows the liposome suspension to be sterilized by filtration through a conventional depth filter, typically a 0.22 micron filter. The filter sterilization method can be carried out on a high through-put basis only if the liposomes have first been sized down to about 0.2-0.4 microns.

Several techniques are available for sizing liposome to a desired size. Sonicating a liposome suspension either by bath or probe sonication produces a progressive size reduction down to small unilamellar vesicles (SUVs) less than about 0.05 microns in size. Homogenization is another method which relies on shearing energy to fragment large liposomes into smaller ones. In a typical homogenization procedure, MLVs are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposome through a small-pore polycarbonate membrane or an asymmetric ceramic membrane is an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size.

D. Removing Free Drug

Even under the most efficient encapsulation methods, the initial sized liposome suspension will contain up to 50% or more gentamicin in free (non-encapsulated) form. Therefore, in order to maximize the advantages of liposomal gentamicin, it is important to remove free gentamicin from the final injectable suspension.

Several methods are available for removing non-entrapped compound from a liposome suspension. In one method, the liposomes in the suspension are pelleted by high-speed centrifugation leaving free compound and very small liposomes in the supernatant. This approach is followed in Example 1, where several liposome washings are employed. Another method involves concentrating the suspension by ultrafiltration, then resuspending the concentrated liposomes in a drug-free replacement medium. Alternatively, gel filtration can be used to separate large liposome particles from solute molecules.

Following treatment to remove free drug, the liposome suspension is brought to a desired concentration for use in intravenous administration. This may involve resuspending the liposomes in a suitable volume of injection medium, where the liposomes have been concentrated, for example by centrifugation or ultrafiltration, or concentrating the suspension, where the drug removal step has increased total suspension volume. The suspension is then sterilized by filtration as described above.

E. Stability of Gentamicin Liposomes

Gentamicin liposomes formed by solvent injection, according to above-described methods, were examined for stability over a 270-day storage period at 4° or 25° C. The results are detailed in Example 2, with reference to FIGS. 1A–1D, where data points for 4° or 25° C. are indicated by open and closed circles, respectively. As seen in FIG. 1A, the total amount of gentamicin in the liposome suspension remained substantially constant during the storage period, indicating little or no drug degradation. Likewise, as seen in FIG. 1B, the percent of free gentamicin in the suspension remained constant at about 2.5% over the storage period, at both storage temperatures. Mean particle size, initially about 1 micron, was also substantially constant over the storage period at 4° C., and fell slightly at 25° C. (FIG. 1C). Percent phospholipid hydrolysis, as measured by changes in the chromatographic pattern of isolated liposomal lipids, was substantially unchanged at 4° C., over the storage period, but rose from about 2% to 6% at 25° C. The results indicate that the gentamicin liposomes are stable on storage in aqueous suspension over at least nine-month storage periods, at refrigerator temperature.

II. Utility

This section examines the biodistribution and efficacy of gentamicin-liposomes when injected intravenously. The observed properties indicate that (a) liposomes cause a much slower release of gentamicin from the body than observed for free drug, and (b) liposomes potentiate the bactericidal action of gentamicin against MAC infection in both the bloodstream and RES tissues.

A. Biodistribution

The distribution of gentamicin in three organs was examined at intervals after intravenous administration of gentamicin liposomes, as detailed in Example 3. The three organs examined were spleen, representative of an RES-rich organ; mesenteric lymph nodes, which are known to harbor bacterial infection in macrophages at the node sites; and kidney, which provides a measure of excretion level. The measured weight of tissue, concentration of gentamicin in the tissue, and tissue concentration were measured at 6, 9, and 13 days after intravenous injection, with the results shown in Table I of Example 3. As seen, drug levels in spleen remained high for up to 13 days after drug administration. The result demonstrates that liposome-encapsulated gentamicin is effectively delivered to the organs of the RES, and drug levels remain high for a several-day period following administration.

The drug levels in the lymph nodes were below the levels of detection at each of the tested time periods. Although the result suggests relatively low uptake of drug by macrophages in the lymph nodes, additional experiments carried out in support of the invention indicate that gentamicin-liposomes are partially effective in reducing bacterial infection in the lymph nodes. Specifically, animals infected with *Salmonella dublin* were treated with increasing doses of gentamicin liposomes by intravenous injection. At day 25 after injection, the level of infection in spleen, lymph nodes, and Peyer's Patches was examined. The gentamicin treatment substantially eliminated infection in spleen at 20 mg/kg dose, and reduced infection levels (colony-forming units or cfu's) in the lymph nodes from about $10^6$ cfu's down to about $10^2$–$10^3$ cfu's at the 20 mg dose.

The level of gentamicin in the kidneys provides a measure of availability of drug in the bloodstream. As seen from the data in Table I, the level of drug in the kidneys was high at day 6, but fell off sharply by day 9. The level of drug retention in the bloodstream provided by the liposomal formulation can be appreciated from drug excretion studies carried out in support of the invention, comparing rates of excretion of amikacin (which was also shown to have organbiodistribution characteristics similar to that of gentamicin) administered in free and liposomal form. As reported in Example 3, the drug was about 80% excreted after four days when given in free form, but more than half of the drug was retained after 12 days when given in liposomal form.

B. Efficacy in Treating MAC Infection

The efficacy of gentamicin liposomes against MAC was tested in immune-deficient mice, specifically C57B16J/bgj strain, as a model of efficacy against MAC infection in immune-deficient individuals. The protocol for animal infection and treatment with free gentamicin and gentamicin-liposomes are given in Example 4. Briefly, the animals were infected by I.V. injection of MAC, then treated with control, gentamicin, or gentamicin-liposome formulations 7 days later, with a total of five intravenous injections being given over a 9-day treatment period. The level of viable MAC units (cfu's) in the blood was examined at day 7 (before treatment), day 16 (immediately after the five treatment doses) and day 22. For comparative purposes, parallel studies were carried out with amikacin, an aminoglycoside whose minimum inhibitory concentration against MAC infection (strain 101 serotype 1) in bacterial culture is nearly an order of magnitude less than that of gentamicin. For both aminoglycoside drugs, dosages of 0.2 mg and 1.0 mg drug were given.

Figure 2A:
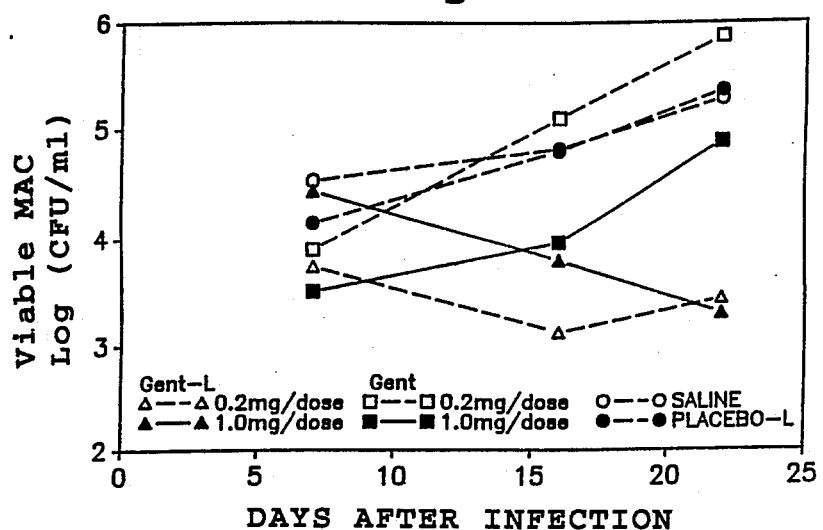
FIGS. 2A and 2B are semi-log plots of viable MAC units in blood as a function of days after infection of immune-deficient mice also known as "beige" mice, after I.V. administration of the control, gentamicin (2A) and amikacin (2B) formulations indicated.
Figure 2B:
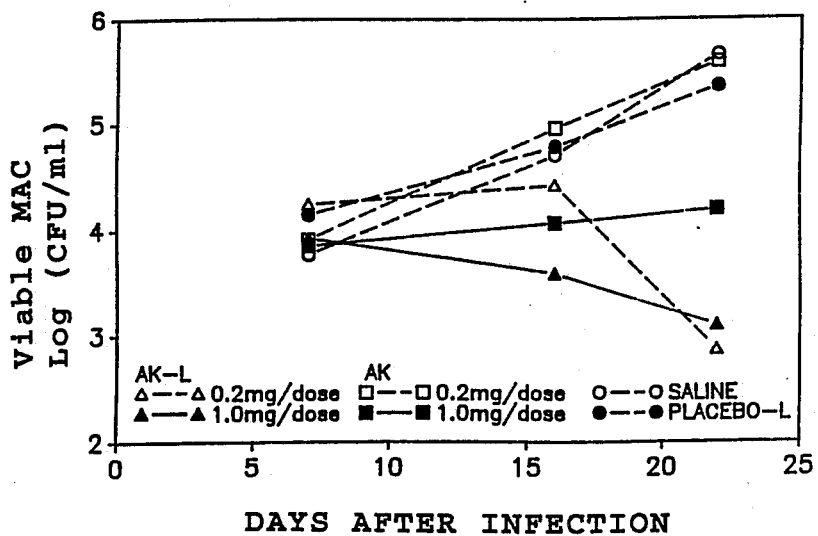

FIG. 2A shows the changes in viable MAC units (log scale) in the blood. The number of infective units increases about two orders of magnitude from day 7 (before treatment) to day 22. No appreciable inhibition is seen in animals treated with saline, empty liposomes, or either 0.2 or 1 mg free gentamicin. By contrast, gentamicin-liposomes produced a strong bacteriocidal effect at both doses. Qualitatively similar results were obtained with free and liposomal amikacin, as seen in FIG. 2B.

Figure 3A:
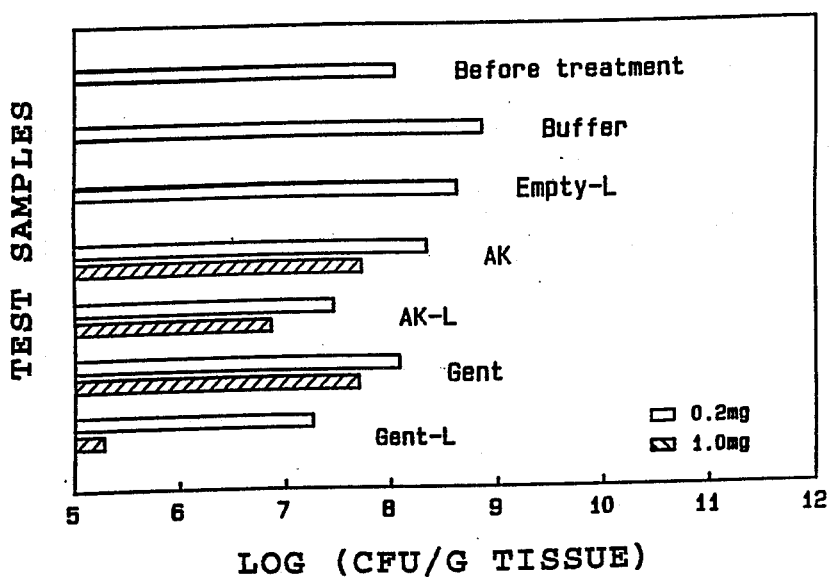
FIGS. 3A and 3B are bar graphs showing viable MAC units in liver or spleen (log scale) after I.V. administration of immune-deficient mice with the control, gentamicin, and amikacin formulations indicated, 22 days after infection, for liver (3A) and spleen (3B).

The treated animals were also examined, at day 22, for level of MAC infection in liver and spleen, with the results shown in FIGS. 3A (liver) and 3B (spleen). As seen, free gentamicin gave about the same degree of bacteriocidal action as free amikacin. However, a comparison of the liposome-drug treatment data shows that gentamicin-liposomes, particularly at the higher dose, gave a substantially greater bacteriocidal action than amikacin-liposomes. In the case of liver, the difference in efficacy was more than 35 fold ($1.9 \times 10^5$ cells vs. $7.3 \times 10^6$ cells). In the case of spleen, the difference in efficacy was more than 15 fold ($1.4 \times 10^6$ cells v. $2.2 \times 10^7$ cells). Summarizing:

1. Free gentamicin, even at relatively high dose, has no measurable activity against MAC in the bloodstream, and only modest activity against infection in RES organs. In this respect the drug effect is similar to that observed for free amikacin at low dose. At the higher dose, amikacin, but not gentamicin shows a significant inhibitory effect on MAC in the blood, consistent with the greater activity of amikacin in free form against MAC in culture.

2. Gentamicin-liposomes produce a strong bacteriocidal effect on MAC in the blood, again substantially equivalent to the effect observed for amikacin.

3. The bactericidal effect of gentamicin in liposomal form is several fold greater than that of amikacin-liposomes, at equivalent drug doses, in organs of the RES.

Thus, although free gentamicin is substantially less active than free amikacin in MAC culture, as discussed above, in liposomal form it is several times more active against MAC infection in RES-rich organs, and substantially as active against MAC infection in the bloodstream.

Gentamicin-liposomes were also substantially less toxic to treated animals than free drug. This was confirmed by attempting to further reduce MAC infection by administering higher gentamicin dose. At a dose of about 4 mg per 20 gm mouse, the gentamicin-liposome formulation was well tolerated, but the free form of the drug resulted in a large percentage of animal deaths.

C Therapeutic Uses of Gentamicin-Liposomes

M. avium complex is a significant cause of serious infection in patients suffering from AIDS. There is growing evidence that effective treatment can prolong the life of infected patients for more than a year after infection, with continuous chemotherapy (Young, 1988). Currently, MAC is treated by intravenous administration of a combination of drugs with known in vitro activity against MAC. One of the most effective combination of agents which have been identified to date is clofazamine and amikacin (Young, 1988). Typically, the drug combination is administered 2-3 times a day until the level of infection is reduced to a suitable maintenance level. At this stage, one or both drugs are administered twice a day, at a dose level required to keep the infection at an acceptably low level.

The present invention is designed to provide a more effective and convenient method of treating MAC infection in immuno-compromised patients. The studies presented above show that gentamicin in liposomal form has a much longer half-life in the body than the free drug, and is effective when administered every two days. Thus, during the initial phase of treatment, drug dosing can be reduced from 2-3 times a day, as currently required for free drug, to once every 1-3 days or even less frequently. The usual I.V. dose level for gentamicin is between about 1-3 mg/kg body weight/day, administered every 8-12 hours. Assuming the drug is administered in liposomal form is administered every 2 days, a drug dose of between about 2-6 mg drug in gentamicin-liposomes would be equivalent. Higher doses are possible, e.g., up to 10 mg or higher, since the liposomes reduce the toxicity of the drug. The injected gentamicin-liposome formulation can be coadministered with other anti-MAC drugs, such as clofazamine. The co-administered drug is preferably one which is active against infection resident in the lymph nodes, since the gentamicin liposomes are least effective at this tissue site.

As seen from the studies above, the liposomal form of gentamicin is effective against MAC infection in the blood, whereas free gentamicin (and amikacin) is largely ineffective. Surprisingly, the gentamicin is substantially more effective against MAC infection in the RES than amikacin-liposomes, and substantially more effective than either free gentamicin or amikacin. Thus initial therapy in drug amounts needed to reduce systemic levels of infection would be accompanied by a greater reduction in viable MAC infection in the liver and spleen.

The following examples are intended to illustrate, but not limit, the scope of the invention.

MATERIALS

Partially hydrogenated egg phosphatidylcholine (PH EPC), egg phosphatidylglycerol (95% pure) (EPG), cholesterol, and alpha-tocopherol were purchased from Asahi Chemical Co., Avanti Polar Lipids, Croda Inc. and Hoffman La Roche, respectively. Gentamicin sulfate, amikacin sulfate, and sodium citrate were purchased from Sigma Chemical Co.

EXAMPLE 1

Preparation of Gentamicin Liposomes

Gentamicin sulfate (activity: 565 ug per mg solid) or amikacin sulfate (activity: 713 ug per mg solid) was dissolved in 10 mM citrate buffer to give 100 mg drug per ml. The pH was adjusted to 6.0 by addition of NaOH. Osmolality of these solutions was approximately 300 mOsm.

PH EPC (62 mole percent), cholesterol (33 mole percent), egg PG (5 mole percent), and alpha tocopherol (0.1 mole percent) were dissolved in 270 ml of Freon, to a final lipid concentration of 50 micromole/ml or 100 micromole/ml.

The lipid mixture was dissolved in Freon TM 11 and slowly injected into the gentamicin solution under partial vacuum with controlled stirring at 20° C. The rate of solvent introduction was about equal to the rate of removal by vacuum. After all the Freon solution was injected, stirring under vacuum was continued until the Freon was removed. The preparation was extruded two times through a one-micron poly carbonate membrane.

The liposomes were washed with citratebuffered saline by centrifugation four times at 200,000 X g for 45 minutes at 4° C. The liposome preparations before and after the washings were assayed for gentamicin (or amikacin) concentration by the Emit assay supplied by Syva, Inc. (Palo Alto, Calif.) (de Porceri-Morton) after lysis in 1% Triton X-100 TM solution for 30 minutes at room temperature. The phospholipid concentration was determined by standard phosphate assay (Barlett, 1959).

The final concentration of liposomes in the suspension was adjusted to a convenient concentration for injection. The loading factor was 215 μg gentamicin or 267 μg amikacin/mg lipid, and about 95% of the drug was associated with liposomes.

EXAMPLE 2

Stability of Gentamicin Liposomes

For the stability studies, samples of buffer, empty (non-drug-containing) liposomes, free gentamicin solution, and gentamicin-liposomes (prepared as in Example 1) were stored in sterile amber vials in the dark at 4° C. and 25° C. At appropriate time points, up to 270 days, duplicate vials at each temperature were assayed. Total and percent free gentamicin were determined as follows: 0.2 ml of gentamicin-liposomes at 50 to 100 μmole lipid per ml were aliquoted in duplicate at 7×20 mm Beckman centrifuge tubes. The tubes were centrifuged at 200,000 g for 60 minutes at 4° C. Greater than 99% of the liposomes were pelleted. The supernatant and pellet were assayed for the gentamicin using the appropriate EMIT assay. The amount of gentamicin found was expressed as the ratio of total gentamicin in the supernatant and pellet. The recovery of this procedure is in the range of 93 to 101%.

Particle size and size distribution were measured by the Coulter Multichannel Counter Model TAII. Total phospholipid and phospholipid subclasses of fractions from silica gel thin layer chromatography were analyzed by the Barlett method as modified by Marinetti from each of the four samples.

The level of gentamicin, including both free and liposomal drug, was measured over a 270 day period to confirm that the drug itself is stable in the liposome preparation. As seen from FIG. 1A, the total gentamicin concentration remained constant (about 3 mg/ml, as detected by immunoassay) over the storage period at both 4° C. and 25° C.

The leakage of gentamicin from liposomes on storage was examined as detailed above, by pelleting the liposome suspension and measuring the gentamicin associated with the pelleted and supernatant fractions. The results are seen in FIG. 1B, showing that the percent free gentamicin measured in the supernatant did not increase with time at either storage temperature, i.e., about 97% of the drug remained associated with the liposomes.

The mean particle size of the gentamicin liposomes over the 270 days storage period is seen in FIG. 1C. Mean particle size decreased slightly at both 4° C. and 24° C. The size distribution profile of the gentamicin liposomes at 4° C. was substantially unchanged, and in the samples stored at 25° C., the particle size distribution shifted slightly to smaller particles. The pH of the formulations remained unchanged during the storage period.

FIG. 1D shows the percent change in lipid composition —reflecting lydrolysis of liposomal lipid during the storage period. Hydrolysis of the phospholipid into lyso-compounds was not detectable at 4° C. There appeared to be a small amount of phospholipid hydrolysis at 25° C. No significant change in the fatty acyl composition was observed (data not shown).

EXAMPLE 3

Biodistribution of Liposomal Aminoglycoside

A. Organ Distribution

Gentamicin-liposomes, prepared as in Example 1, were administered intravenously to 8 mice at a dosage of 10 mg/kg each. At 6, 9 and 13 days after administration, injected animals were sacrificed and spleen, lymph nodes and kidneys were removed, washed, and assayed for gentamicin. Organ weights and gentamicin concentrations are shown in Table I below. The values for days 6 and 9 are the mean of three mice and the day-13 values are the mean of 2 mice.

TABLE 1

|         | Day 6      |                  |      | Day 9      |                  |      | Day 13     |                  |      |
|---------|------------|------------------|------|------------|------------------|------|------------|------------------|------|
| Organs  | Wt. (mg)   | Gent (mg/ml)     | Conc | Wt. (mg)   | Gent (mg/ml)     | Conc | Wt. (mg)   | Gent (mg/ml)     | Conc |
| Spleen  | 151        | 11.3             | 150  | 216        | 7.5              | 70   | 117        | 8.0              | 130  |
| Nodes   | 53         | <1               | <1   | 54         | <1               | <1   | 28         | <1.0             | <1   |
| Kidneys | 115        | 1.3              | 20   | 125        | 0.4              | 10   | 77         | <1.0             | <1   |

Concentration given in μg/gm tissue

As seen, the concentration of gentamicin remained high in spleens for 13 days after treatment. No animal had detectable amounts of gentamicin in its mesenteric lymph nodes. Gentamicin was detected in all three kidneys removed on day 3, in a third of the kidneys removed on day 9 and in 0/3 on day 13, suggesting a decline in gentamicin excretion despite a persistence of gentamicin in the spleen throughout the experimental period. Similar biodistribution and drug persistence values were obtained with I.V. administered amikacin-liposomes, prepared substantially as in Example I, but substituting amikacin for gentamicin.

B. Renal Clearance

As indicated above, the organ distribution of gentamicin-liposomes after I.V. injection is similar to that of amikacin liposomes. To examine the difference in drug clearance between free aminoglycoside and an aminoglycoside-liposome composition, free amikacin and amikacin-liposomes were administered to groups of mice, as above, and the amount of drug excreted by the animals over a several-day period was examined. About 80% of the free drug was excreted after 4 days. By contrast, only about 40% of the drug administered in liposomal form was excreted.

EXAMPLE 4

Efficacy of Aminoglycoside Liposomes Against MAC Infected "Beige" Mice

Immune deficient "beige" mice (Young, 1986) were infected intravenously with $5 \times 10^6$ of MAC 101 (serotype 1) on day 0. After 7 days, blood samples were drawn to quantitate the organisms in the blood prior to treatment. The mice (10 mice per group) were injected intravenously with the control, gentamicin, and amikacin formulations indicated in FIGS. 2A, 2B, 3A, and 3B, every other day until they had received five samples. On the 16th day, the treated mice were bled and the number of viable MAC units in blood was determined. A week later (day 22), the mice were bled again and sacrificed. The liver and spleen were homogenized and the viable MAC were cultured in 7H10 agar for 10 days for colony counts.

As seen from FIG. 2A, free gentamicin had no appreciable inhibitory effect on MAC infection in the blood between 7 and 22 days post infection at either dose levels. By contrast, the same doses of gentamicin in liposomal form produced a pronounced bacteriocidal effect, i.e., final cfu's were lower than initial infection values.

Liposomal entrapment also potentiated the anti-bacterial effect of amikacin on MAC in the blood, as seen in FIG. 2B.

Figure 3B:
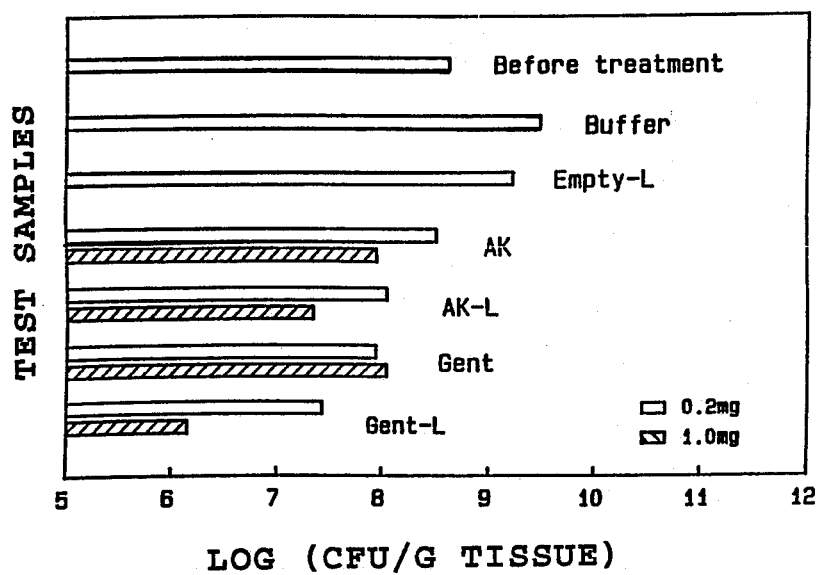

The number of viable MAC in the livers and spleens was measured after treatment with the control, gentamicin, and amikacin formulations given in FIGS. 3A and 3B. On day 7 after infection, the liver and spleen had about $10^8$ MAC per ram of tissue. The group of infected "beige" mice treated with the buffered saline showed a 5-6 fold increase in MAC in both the liver and spleen. Treatment with the empty liposomes slightly diminished the percent increase in MAC in these organs. Free gentamicin solution showed inhibitory effect on the growth of MAC in the liver at the low dose (0.2 mg/kg) and moderate killing activity at the high dose (1.0 mg/kg), and both doses produced moderate killing of MAC in the spleen.

When compared with equivalent doses of free gentamicin, gentamicin-liposome treatment produced about 1/6th the number of viable MAC at 0.2 mg and about a 1/263rd the number of viable MAC at 0.1 mg dose in the liver. The level of reduction was about 1/3rd the number of viable MAC at 0.2 mg and about 1/78th the number at 1 mg in the spleen.

Liposome potentiation of amikacin activity was significantly less than for gentamicin, particularly at the higher dose levels, in both liver and spleen.

Although the invention has been described with and respect to specific formulations and treatment methods, it will be appreciated that various changes and modifications can be made without departing from the invention.

What is claimed is:

1. A method of treating a subject having infectious levels of *Mycobacterium avium* Complex in the bloodstream and in the reticuloendothelial tissue, comprising
    providing a suspension of liposomes containing entrapped gentamicin,
    administering intravenously to the subject the suspension containing an amount of gentamicin which is equivalent to a therapeutically effective amount of amikacin, when the amikacin is administered intravenously in liposome-entrapped form.
    repeating said administering, at dosing intervals of about once every 24 hours or more, until the level of infectious Complex in the bloodstream has been significantly reduced, and
    by said repeated administering, achieving a reduction in the level of the Complex in the bloodstream which is similar to, and a reduction in the level of the Complex in the reticuloendothelial tissue which is several fold greater than, that which would be achieved by repeated administration of such therapeutically effective amount of amikacin, in liposome-entrapped form.

2. The method of claim 1, wherein the amount of liposome-entrapped gentamicin which is administered is between about 1-10 mg/kg body weight.

3. The method of claim 1, wherein the liposomes contain between about 50-80 mole percent phosphatidylcholine, between about 20-50 mole percent cholesterol.

4. The method of claim 1, wherein the liposomes contain between about 1-10 mole percent gentamicin.

* * * * *

UNITED STATES PATENT AND TRADEMARK OFFICE
CERTIFICATE OF CORRECTION

PATENT NO. : 4,952,405

DATED : August 28, 1990

INVENTOR(S) : Annie Yau-Young

It is certified that error appears in the above-identified patent and that said Letters Patent is hereby corrected as shown below:

ON TITLE PAGE:

In the References, Column 1, line 32, change "AntimiCrob." to --Antimicrob--

In the Background, Column 1, line 40, change "infeCtions" to --infections--.

In the Description, Column 4, line 29, delete "." after Briefly.

In the Description, Column 8, line 18, change "coadministered" to --co-administered--.

In the Examples, Column 9, line 1, change "citratebufferred" to --citrate-buffered--.

In Claim 1, Column 12, line 21, delete "." after form and add --,--.

In Claim 3, column 12, line 39, after the "," add --between about 5-15 mole percent phosphatidylglycerol and--.

On the cover page, under Section [56] "References Cited" and under "U.S. PATENT DOCUMENTS", insert the following:

--4,522,803  6/1985  Lenk et al. ..........424/1.1--.

Signed and Sealed this

Thirty-first Day of December, 1991

Attest:

HARRY F. MANBECK, JR.

*Attesting Officer*     *Commissioner of Patents and Trademarks*